United States Patent [19]

Wetzel

[11] 4,130,121
[45] Dec. 19, 1978

[54] POLYETHER POLYURETHANE FOAM END WRAP TREATED WITH BUFFER SYSTEM

[75] Inventor: Thomas A. Wetzel, Cincinnati, Ohio

[73] Assignee: The Procter & Gamble Company, Cincinnati, Ohio

[21] Appl. No.: 783,118

[22] Filed: Mar. 31, 1977

[51] Int. Cl.² ............................................. A45D 7/00
[52] U.S. Cl. ......................................... 132/7; 424/70
[58] Field of Search .............................. 132/7; 424/70

[56] References Cited

U.S. PATENT DOCUMENTS

| | | | |
|---|---|---|---|
| 2,633,447 | 3/1953 | Head | 132/7 X |
| 2,991,790 | 7/1961 | Boncla | 132/7 |
| 3,345,993 | 10/1967 | Haefele | 132/7 |
| 3,955,586 | 5/1976 | Hartsough | 132/7 |

Primary Examiner—G.E. McNeill
Attorney, Agent, or Firm—Douglas C. Mohl; Richard C. Witte

[57] ABSTRACT

A superior permanent hair waving end wrap comprising a particular type of open-celled polyether polyurethane foam of specified porosity and thickness which foam has been treated with a buffer system of monobasic orthophosphate salts in admixture with phosphoric acid. Also disclosed is a permanent hair waving process using said buffer system treated end wraps.

8 Claims, No Drawings

POLYETHER POLYURETHANE FOAM END WRAP TREATED WITH BUFFER SYSTEM

BACKGROUND OF THE INVENTION

1. Field of the Invention

This invention relates to buffer system treated polyurethane foam end wraps for use in the cold permanent waving of hair. Further, the invention relates to the process of using the treated end wraps in cold permanent waving.

2. Prior Art

Cold permanent waving of hair has been a popular means of waving hair for a number of years. This popularity is due to the greater convenience for this method over other methods which require externally applied heat to achieve the desired result. This additional convenience has permitted nonprofessional consumers to wave their own hair at home. In cold waving, the waving is accomplished by applying a reducing agent to the hair which causes the hair to be "softened" (the disulfide linkages present in the keratin of hair are broken). This reducing step may be done after the hair has been sectioned into individual tresses but before it has been rolled onto curlers, after the rolling has been accomplished, or at both times. After sufficient time has elapsed, the hair is rinsed and neutralized by chemical or air oxidation, which step reforms the disulfide linkages broken in the aforementioned reducing step.

Cold permanent waving is not without its problems however. The materials are often difficult to use and/or do not always achieve the desired result. For example, the ends of the hair present particular problems from a handling point of view, as well as from a hair damage point of view. In the waving process, the free ends of the hair must be wound around a cylindrical body (a curler) and this presents some difficulty. Most commercial waving kits overcome this problem by including small square or rectangular pieces of paper or other material (end wraps) which are to be folded and placed around a hair tress in such a manner that they embrace the free end of the tress.

Among the types of materials which have been used for the end wrap are permeable polyester and polyether polyurethanes as disclosed by Haefele in U.S. Pat. No. 3,345,993, issued Oct. 10, 1967; impermeable polyester and polyether polyurethane as disclosed by Haefele in U.S. Pat. No. 3,465,759, issued Sept. 9, 1969; and paper as disclosed by Bonilla in U.S. Pat. No. 2,991,790, issued July 11, 1961. Of these materials, permeable polyurethane foams prepared by condensation of organic isocyanates with polyols are especially useful. Such polyurethanes have excellent solvent resistance and color stability in the presence of ultraviolet light.

All of these types of end wraps which have been disclosed in the prior art are well known to be helpful in the winding process. However, they do not fully protect the ends of the hair. The desirability of protecting the ends of the hair in permanent waving stems from the fact that repeated use of conventional waving procedures is often accompanied by an overexposure of the hair ends which are susceptible to damage because of the age of the hair at the ends and the stress the ends are exposed to during the winding process. Such ends, when subjected to successive cold waving treatments, generally exhibit undue frizziness, curling, harshness and dryness because frequent treatment is believed to unduly stress and overexpose the hair ends in renewing or repeating the waving process.

There have been attempts in the past to treat certain types of end wraps with chemical agents so that the waving solution is counteracted before reaching the hair ends (See, for example, the aforementioned Bonilla reference). Also included in some prior art attempts was the treatment of paper end wraps with citric acid to counteract the waving solution and thereby protect hair ends. Prior art end wraps even include end wraps treated with buffer systems as disclosed by Hartsough in U.S. Pat. No. 3,955,586, issued May 11, 1976. However, those buffer treated end wraps were limited to buffer systems having a pH of greater than 3.0.

It has been surprisingly discovered that hair end wraps treated with buffer systems having a pH of less than 3.0 are superior in protecting hair ends from damage when undergoing cold waving treatment.

While it would be highly desirable to treat end wraps with waving solution counteractant such as buffer systems providing a pH of less than 3, certain of such common counteractant chemicals are not compatible with all types of end wrap polyurethane. Some agents such as citric acid, for example, tend to degrade and discolor certain polyurethanes. There is, therefore, a continuing need to identify and select compatible materials for use in realizing preferred buffer system treated end wraps for cold permanent waving products and methods.

Accordingly, it is an object of this invention to provide superior buffer system treated end wraps treated with buffer systems having a pH of less than 3 and which are useful in the keratin modification process.

Accordingly, it is a further object of this invention to provide such treated end wraps which are made with preferred compatible end wrap and buffer system treatment materials.

It is a further object to provide an improved method for permanently waving hair by utilizing treated end wraps made from perferred materials.

It has been surprisingly discovered that by selecting polyether polyurethane end wraps for treatment with specific buffer systems, the above objectives can be realized and end wraps prepared which are superior to similar articles of the prior art.

SUMMARY OF THE INVENTION

The present invention is directed to end wraps for use in cold permanent waving processes. The end wraps comprise permeable, flexible wafers of open-celled polyether polyurethane foam containing a buffer system which is present to the extent of at least fifty milligrams per cubic inch of foam. The buffer system comprises a mixture of a mono-basic orthophosphate salt and orthophosphoric acid wherein the weight ratio of the phosphate moiety of the phosphate salt to the phosphate moiety of the orthophosphoric acid ranges from about 3:1 to about 5.4:1. This buffer system provides a pH ranging from about 2.5 to about 2.9.

The foam wafers have a thickness ranging from about one-sixteenth inch to about one-sixty-fourth inch and an average pore incidence of from about 30 to about 120 pores per linear inch.

The present invention is also directed to a process for imparting a permanent wave to hair. Such a process comprises the steps of forming hair into tresses, wrapping about the end of each tress a flexible, acid treated end wrap of the type described above, winding each tress on a cylindrical body, saturating each wound tress with a keratin-reducing composition and thereafter neutralizing the action on the hair of said keratin reducing composition.

DETAILED DESCRIPTION OF THE INVENTION

The present invention resides in the discovery of an improved hair waving end wrap comprising a particular type of porous polyether polyurethane foam wafer treated with specific, solid, water-soluble buffer systems having a pH ranging from about 2.5 to about 2.9.

Each component of the improved end wrap treated with the specific buffer systems herein as well as end wrap preparation and method of cold permanent hair waving are described in detail as follows:

Polyether Polyurethane Foam End Wraps

It has been surprisingly discovered that specific "polyether" polyurethane foam materials are suitable for end wraps treated with specific low pH buffer systems (pH 2.5–2.9). Polyurethane foams are in general prepared by condensing polyols with organic isocyanates. Such polyurethane foams are divided in two major categories depending on the type of polyol used in preparation — either "polyether" polyols or "polyester polyols". Of these two types, "polyether" polyurethane foams are the materials used in this invention. For purposes of this invention, a polyether polyurethane refers to a polyurethane made from a polyether polyol and an organic isocyanate.

It has been discovered that only "polyether" polyurethane foams are suitable for use herein because polyether polyurethane foams are not subject to the same degree of chemical degradation at the low pH's provided by the instant buffer systems as are analogous polyester foams. It is speculated that acid hydrolysis of the ester linkages of the polyester polyurethanes results in chemical degradation under low pH conditions thereby leading of loss of end wrap structural integrity and strength. The ether linkages of the polyether polyurethane appear resistant to acid hydrolysis and are thus not as subject to such undesirable chemical degradation.

The polyether polyurethane foams of the present invention can be prepared by a variety of methods well known in the art. Essentially, such foams are made by the condensation of organic isocyanates, such as toluene diisocyanate, with polyethers such as the reaction product of propylene oxide and glycerol in the presence of a catalyst, surfactant and perhaps a blowing agent. Basic apparatus, processes and starting materials for preparing such polyether polyurethane foams are disclosed, for example, in Hoppe et al., U.S. Pat. No. 2,764,565; issued Sept. 25, 1956; Lamplugh et al.; U.S. Pat. No. 3,772,218; issued Nov. 13, 1973; Lamplugh et al., U.S. Pat. No. 3,799,898; issued Mar. 26, 1974; Fishbein et al.; U.S. Pat. No. 3,879,316; issued Apr. 22, 1975 and Ridenour et al.; U.S. Pat. No. 3,880,780; issued Apr. 29, 1975. All of these patents are incorporated herein by reference.

The polyether polyurethane foam end wraps used as the starting material for this invention are the polyether analogs of the polyester polyurethane end wraps exemplified in U.S. Pat. No. 3,345,993, Oct. 10, 1967, to Haefele incorporated herein by reference. These end wraps are preferably either square or rectangular in shape and have dimensions within the range from $1\frac{3}{8} \times 1\frac{3}{8}$ inches to $4 \times 4$ inches. An especially preferred size and configuration is a rectangular wafer having the dimensions $3 \times 2$ inches.

The thickness of the untreated foam end wraps can vary within the range of one-sixty-fourth to one-sixteenth inch. As the length and width are increased, a thinner end wrap should be used. Foam end wraps which are thinner than about one-sixty-fourth inch are difficult to process and do not have sufficient tear strength for the intended use. End wraps having thicknesses greater than about one-sixteenth inch yield too large a curl. The preferred thickness for the purpose of this invention is one-thirty-second inch.

The degree of porosity of the end wrap must be sufficient to permit substantially unimpeded flow of the waving and neutralizing solutions. An average pore incidence from about 30 to about 120 pores per linear inch is necessary for adequate flow. More numerous pores are preferable in the case of thinner end wraps. The preferred end wraps have an average of about 80 pores per linear inch.

Buffer System

The polyether polyurethane foam end wraps are treated with a buffer system which counteracts the effects on hair ends of the keratin-modifying solution employed in cold permanent waving. The buffer systems of this invention comprise mixtures of (1) a water-soluble, mono-basic orthophosphate salt and (2) a mineral acid which is orthophosphoric acid, $H_3PO_4$. Such buffer systems are solid, have pH's ranging from about 2.5 to about 2.9 (said pH being the pH of a 25° C. aqueous solution of the buffer system mixture at a concentration of from about 0.2% up to the solubility limit of said buffer system); and have a salt phosphate moiety to acid phosphate moiety weight ratio ranging from about 3:1 to about 5.4:1.

The orthophosphate salts useful herein are derived from tribasic orthophosphoric acid of the formula $H_3PO_4$. Water-soluble sodium, potassium and ammonium salts can be utilized. Such salts can be either in hydrated or anhydrous form. For purposes of this invention a "water-soluble" orthophosphate salt is one which is soluble in water to the extent of at least 0.2% at 20° C.

Dibasic and tribasic orthophosphate salts are not contemplated for use herein. If such di- and tri-basic salts were employed, relatively large amounts of mineral acid would have to be added to the buffer system to produce buffer systems having a pH within the critical 2.5–2.9 range to provide a high degree of hair end protection. Such high acid buffer systems would not have sufficient buffer capacity at the concentration levels contemplated in the present invention to adequately counteract the effects on hair ends of the keratin-modifying solution.

There are many different crystalline mono-basic sodium orthophosphate salts including the various hydrates. These include, for example, $NaH_2PO_4$, $NaH_2PO_4 \cdot H_2O$, $NaH_2PO_4 \cdot 2H_2O$, and mixtures thereof. Potassium and ammonium mono-basic orthophosphates can also be utilized as the orthophosphate component of the buffer system herein. Examples of such potassium and ammonium salts include $KH_2PO_4$, $(NH_4)H_2PO_4$, hydrates thereof and mixtures of these salts. The soluble mono-basic orthophosphate salts of the present invention are commercially available materials. A more detailed description of the orthophosphate salts useful herein can be found in Kirk & Othmer, *Encyclopedia of*

*Chemical Technology*, Volume 15, Interscience Publishers, Inc. (1954), pp. 234–239, incorporated herein by reference.

Orthophosphoric acid is a common, commercially available material typically sold as an 85% by weight aqueous solution although it is available as a solid. A more detailed description of the orthophosphoric acid useful herein also can be found in Kirk & Othmer, supra.

It has been found that hair end protection is enhanced when the hair end wrap is treated with a solution of the buffer system which has a pH ranging from 2.5 to about 2.9. Utilization of systems providing pH values within this range is thus essential to realization of the high degree of hair end protection contemplated herein. Aqueous solutions of orthophsophate salts, however, have pH's typically ranging from 4 to about 10. Orthophosphoric acid, $H_3PO_4$, is employed herein to lower the pH of the orthophosphate solution to within the desirable pH range.

Suitable buffering systems must not only provide a pH within this critical pH range, but also provide sufficient buffer capacity to counteract the amounts of keratin-modifying solution typically employed in cold permanent waving. Buffer capacity is qualitatively thought of as the quantity of acid or base a buffer system is capable of consuming without an appreciable pH change in the system being buffered. In order to ensure adequate buffer capacity, orthophosphate salts and mixtures thereof are present in the buffer system to the extent such that the weight ratio of phosphate moiety provided by the salt to the phosphate moiety provided by the orthophosphoric mineral acid is from about 3:1 to about 5.4:1, preferably from about 3.6:1 to about 5.4:1.

It has also been found that the amount of orthophosphate salt/orthophosphoric acid buffer system material present in the foam end wraps of this invention can vary depending on the thickness and outside surface area of the wrap. A minimum level of 50 milligrams of buffer system mixture per cubic inch of foam is thought to be required to ensure that protection is obtained. It is preferred, however, that the amount of buffer mixture present be from about 75 milligrams to about 175 milligrams per cubic inch of foam. This range allows the ends of the hair to be adequately protected while still ensuring that they receive some wave.

End Wrap Preparation

The foam end wrap material can be conveniently treated by use of a water solution of the buffer system. The foam material can be passed through the water solution, or the solution can be brushed or sprayed onto the foam material. The treated material is then dried by means of a drum dryer or oven, air exposure or by other suitable means to remove the moisture present. Noxious fumes are not a problem with preparation of the instant end wraps.

The concentration of buffer system in the water solution depends on the materials used, the method of application employed, and the buffer system concentration desired in the treated foam end wraps. The concentration of buffer system in the water solution typically would be in the range of about 0.2% to about 60%. (Of course, the upper limit is subject to the solubility of the buffer system used).

To decrease the likelihood of the end wraps picking up static charge, the foam may be treated with an antistatic material such as a mineral oil mixture.

Hair Waving Method

A preferred embodiment of this invention relates to the process of cold permanent waving. Use of this invention's buffer system-treated foam end wraps in the same manner as conventional end wraps in cold permanent waving reduces the strength of the wave given to the ends of the hair. This is believed to be due to the lowering of the pH of the reducing solution when it comes into contact with the treated foam end wrap which is around the ends of the hair. This results in a softer looking wave, with greater fullness, but with the same strength of curl as current products give except at the hair tips.

More specifically, in regard to the aspect of cold permanent waving processes, this invention comprises the steps of forming the hair into tresses, wrapping around the end of each tress a treated foam end wrap of the type disclosed herein, winding each tress about a cylindrical body, i.e., a curler, saturating each tress with a keratin-reducing composition and thereafter neutralizing the action on the hair of said keratin-reducing composition. Alternatively, the keratin-reducing composition is applied to the hair both before and after the hair is rolled upon curlers.

The keratin-reducing compositions which can be used in the permanent wave processes of this invention contain a water-soluble, nonvolatile mercaptan such as mercapto-alkanoic acids, mercapto-acetic acid, mercapto-propionic acid, mercapto-butyric acid and water-soluble salts thereof. Examples of other suitable mercaptans are thioglycolic acid, sodium thioglycolate, potassium thioglycolate, monoethanolamine thioglycolate, $\beta$-mercapto isobutyric acid, thiohydracrylic acid, $\beta$-mercapto-n-butyric acid, mercapto-caproic acid, thioglycerol and thiolactic acid. These compositions have a pH of 7.0 to 9.5 which can be provided with alkaline agents such as ammonia, monoethanolamine, diiospropylamine, sodium hydroxide, potassium hydroxide and the like.

In addition to the mercaptans, it is often desirable, but not essential, to include in the keratin-reducing composition a water-soluble disulfide of the mercaptan used such as dithiodiglycolic acid, dithiodilactic acid, the disulfides of $\beta$-mercaptobutyric acid, $\beta$-metcaptoisobutyric acid, dithiodihydracrylic acid or a water-soluble salt of these acids to protect against excessive reduction and damage to the hair in accordance with the disclosures in U.S. Pat. No. 2,719,814, Oct. 4, 1955, to Haefele and U.S. Pat. No. 2,719,815, Oct. 4, 1955, to Sanders.

The permanent waving processes of this invention can also be used to advantage in conjunction with pressurized hair waving compositions which are applied to the hair as a fast-breaking foam. Examples of such compositions are disclosed by Banker et al. in U.S. Pat. No. 3,099,603, July 30, 1963, and Sheperd et al. in U.S. Pat. No. 3,103,468, Sept. 10, 1963.

The action on the hair of the keratin-reducing compositions can be neutralized by chemical compounds such as bromates, perborates, hydrogen peroxide or the action of air alone.

End Wrap Exemplification

Certain particular embodiments of the invention are illustrated in the following examples but the invention is not intended to be limited thereto. All percentages used herein previously and subsequently are by weight unless otherwise indicated.

EXAMPLE I

A polyurethane-foaming reaction mixture of the following composition is prepared:

| Component | Parts by Weight |
|---|---|
| PROPYLAN 555*Polyether Triol | 100 |
| C-6**Catalyst | 0.6 |
| N-Ethylmorpholine Catalyst | 0.1 |
| Water | 3.0 |
| Toluene Diisocyanate (80:20 Mixtures of 2,4- and 2,6-isomers) | 31.6 |
| L-532***Surfactant | 3.0 |

*Condensation product of propylene oxide and ethylene oxide with glycerol (60% - 70% terminal hydroxyl groups; Molecular weight = 5000)
**Solution of one part (wt.) stannous octoate and two parts (wt.) dioctylphthalate - Witco
***Polyoxyalkylene-siloxane copolymer - Union Carbide The above mixture is hand mixed at room temperature and is poured into an aluminum mold provided with a clamped lid. The mixture is maintained within the temperature range of 140°-150° F. Foaming is complete in about three minutes. The resulting foam is allowed to cure at ambient temperature.

The product is a slab of flexible polyether polyurethane foam of 2.3 pounds per cubic foot density, having an average of 60 cells per linear inch. The slab is then cut into 3 × 2 inch wafers or larger sheets having a thickness of one-thirty-second inch.

The reactants and conditions as identified above can be varied in accordance with the teachings of Hoppe et al., U.S. Pat. No. 2,764,565, issued Sept. 25, 1956 and Lamplugh et al., U.S. Pat. No. 3,799,898; issued Mar. 26, 1974, to yield foams having an average of 40, 80 and 120 pores per linear inch and thicknesses of one-sixteenth and one-sixty-fourth inch.

EXAMPLE II

Foam end wraps measuring 3 × 2 × 1/32 second inch made according to Example I are dipped into a 3% by weight aqueous solution of mono-basic sodium orthophosphate and phosphoric acid having a pH of 2.8. The 3% solution was prepared by adding 25 grams of mono-basic sodium orthophosphate monohydrate and 5 grams of orthophosphoric acid (85% by weight $H_3PO_4$ in water) to 970 grams of water. The amount of solution absorbed by each foam end wrap is 1.1 grams (corresponding to about 125 milligrams of acid/cubic inch of foam). The wraps are then allowed to air dry for a period of about 16 hours at room temperature (~75° F.).

Buffer system treated end wraps so produced can be used in effective permanent hair waving processes with minimal damage to hair ends treated thereby.

EXAMPLE III

A sheet of polyether polyurethane foam measuring 15¾ × 18¾ × 1/32 inch made according to Example I is dipped into a 3.0% solution of mono-basic sodium phosphate monohydrate and orthophosphoric acid having a salt phosphate moiety to orthophosphoric acid phosphate moiety weight ratio of about 4.14:1 and a pH of 2.8. The solution is prepared by mixing 25 grams of $NaH_2PO_4 \cdot 1H_2O$ and 5 grams $H_3PO_4$ into 970 grams water. The sheet is wrung out until 8.0 grams (corresponding to about 138 milligrams of buffer system/cubic inch of foam) of the solution are still retained. The sheet is then air dried for a period of about four hours at room temperature (~75° F.). As a final step, individual end wraps measuring 3 × 2 × 1/32 inch are cut from the sheet. Such end wraps are especially useful in premanent hair waving processes.

Substantially similar buffer system treated polyether polyurethane end wraps are realized when in the above Example III the mono-basic sodium orthophosphate is replaced with an equivalent amount of anhydrous mono-basic sodium orthophosphate, $NaH_2PO_4$, anhydrous mono-basic potassium orthophosphate, $KH_2PO_4$, anhydrous mono-basic ammonium orthophosphate, $NH_4H_2PO_4$.

EXAMPLE IV

The buffer system treated foam end wraps as prepared in accordance with Example II are employed in a permanent waving process using the following keratin-reducing composition:

| Component | Weight % |
|---|---|
| Monoethanolamine thioglycolate | 11.41 |
| Hydrogen peroxide | 0.34 |
| Monoethanolamine | 2.30 |
| Mineral oil | 1.555 |
| Oleic acid | 0.337 |
| Potassium hydroxide | 0.088 |
| Ethylene glycol | 0.199 |
| Perfume | 0.50 |
| Polyoxyethylene (23) lauryl ether | 1.043 |
| Color | 0.10 |
| Distilled water | 82.128 |
| | 100.000 |

The hair is washed and separated into tresses. The buffer system treated end wrap is folded over the wet hair tress so that it covers all of the free ends. Each wrapped tress is then wound upon a curler and secured. The keratin-reducing composition is applied to the wound tresses and after waiting 15 minutes, rinsed with water and blotted. The head is then covered with a towel and after an additional 30 minutes the hair is neutralized with a 3% hydrogen peroxide solution. The hair is removed from the curlers, again rinsed with water, set in a normal fashion and dried.

We claim:

1. An end wrap for use in the permanent hair waving process, comprising:

A. a permeable flexible wafer of open-celled polyether polyurethane foam having:
  I. a thickness of from about one-sixteenth inch to about one-sixty-fourth inch,
  II. an average pore incidence within the range of from about 30 to 120 pores per linear inch; and B. a solid, water-soluble buffer system contained in said wafer at a level of at least 50 milligrams of buffer system per cubic inch of foam, said buffer system comprising a mixture of:
  I. a water-soluble mono-basic orthophosphate salt, and
  II. orthophosphoric acid, wherein the buffer system has a pH of from about 2.5 to about 2.9 and wherein the weight ratio of phosphate moiety of the orthophosphate salt to the phosphate moiety of the orthophosphoric acid ranges from about 3:1 to about 5.4:1.

2. An end wrap according to claim 1 wherein the wafer of polyether polyurethane foam has a thickness of one-thirty-second inch.

3. An end wrap according to claim 1 wherein the wafer of polyether polyurethane foam has an average pore incidence of 80 pores per linear inch.

4. An end wrap according to claim 1 wherein the mono-basic orthophosphate salt is mono-basic sodium orthophosphate.

5. An end wrap according to claim 4 wherein the buffer system is contained in the wafer at a level of between about 75 and 175 milligrams per cubic inch of foam.

6. An end wrap according to claim 5 wherein the weight ratio of phosphate moiety of the mono-basic orthophosphate salt to phosphate moiety of the orthophosphoric acid ranges from about 3.6:1 to about 5.4:1.

7. The process of imparting a permanent wave to hair which comprises the steps of forming the hair into tresses; wrapping about the end of each tress a permeable, flexible wafer of polyether polyurethane foam having a thickness of from about one-sixteenth inch to about one-sixty-fourth inch and having an average pore incidence within the range of from about 30 to 120 pores per linear inch, said wafer containing at least 50 milligrams per cubic inch of foam of a solid, water-soluble buffer system having a pH of from about 2.5 to about 2.9, said buffer system comprising a mixture of a mono-basic orthophosphate salt and phosphoric acid, whereas the weight ratio of phosphate moiety of the orthophosphate salt to phosphate moiety of the phosphoric acid ranges from 3.1:1 to about 5.4:1; winding each tress on a cylindrical body; saturating each wound tress with a keratin-reducing composition; and thereafter neutralizing the action on the hair of said keratin-reducing composition.

8. A process according to claim 7 wherein the wafer of polyether polyurethane foam has a thickness of one-thirty-second inch and an average pore incidence of 80 pores linear inch.

* * * * *